May 7, 1974 R. L. BYRUM Plant Pat. 3,544
YELLOW ROSE PLANT
Filed Feb. 15, 1973
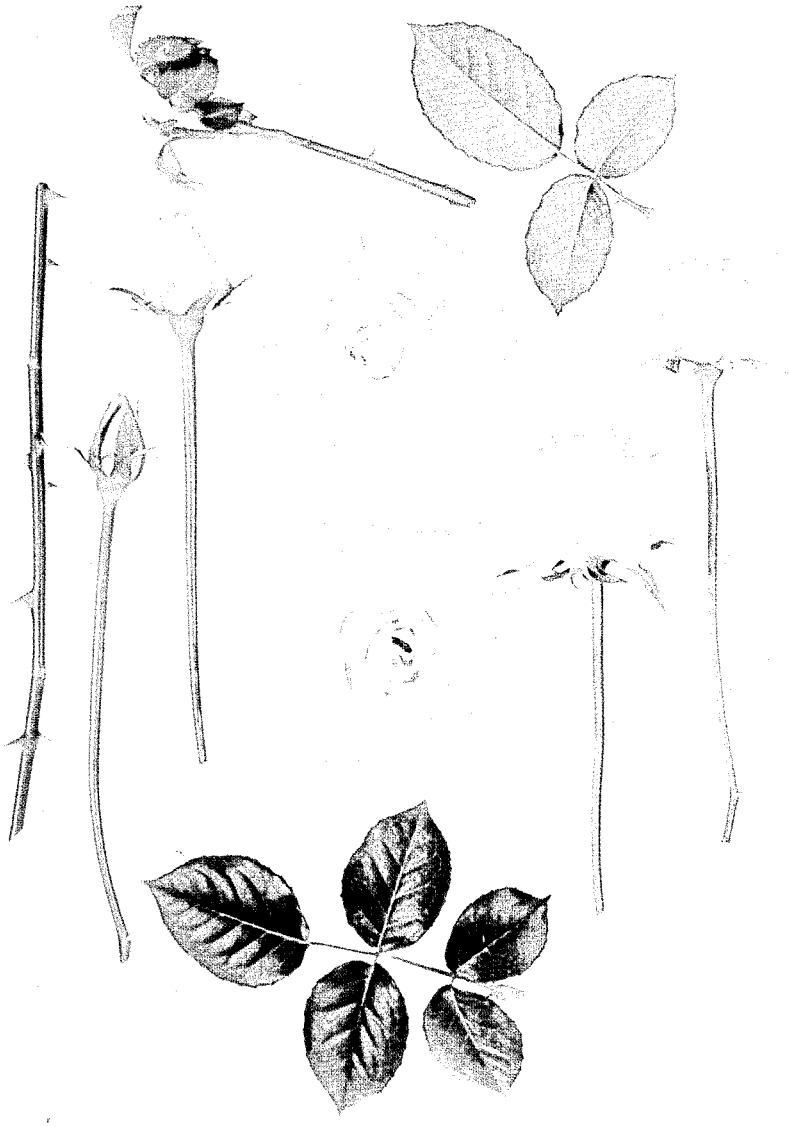

United States Patent Office

Plant Pat. 3,544
Patented May 7, 1974

3,544
ROSE PLANT

Roy L. Byrum, Richmond, Ind., assignor to Joseph H. Hill Company, Richmond, Ind.

Filed Feb. 15, 1973, Ser. No. 332,877
Int. Cl. A01h 5/00
U.S. Cl. Plt.—15 1 Claim

ABSTRACT OF THE DISCLOSURE

A new variety of hybrid tea rose capable of continuous and abundant production under greenhouse culture and distinguished by its vigorous and prolific growth with longer and stronger stems, the more constant intense color of its blooms which does not fade under extreme temperature or low light intensities, and by its improved propagation capabilities.

BACKGROUND OF THE INVENTION

The new variety of rose plant herein disclosed originated as a seedling of Lydia (unpatented) × Golden Wave (P.P. 2,105) crossed by me in March 1965 in the course of breeding efforts carried on by me at Richmond, Ind., with the object of developing better roses for the commercial greenhouse production of cut flowers. This plant was observed to have better characteristics of growth, strength and flower production than its parents and since its first flowering in October 1966, it has shown an ability to maintain a more constant and intense color in its yellow flowers regardless of temperature and light intensity variations. Asexual propagation of this plant by budding at Hamilton City, Calif., and under my direction has demonstrated that the improved characteristics are fixed and hold true from generation to generation.

DESCRIPTION OF THE DRAWING

This new rose plant is illustrated by the accompanying full color drawing which shows the form of the buds, freshly opened and mature blossoms, the characteristics of the wood and young leaves, and the nature of the top and under side of mature leaves, the color of the blossoms being as true as it is reasonably possible to obtain by conventional photographic procedures.

DESCRIPTION OF THE PLANT

The following is a detailed description of this new variety of rose plant with specifications of color according to the Horticultural Colour Chart by Robert S. Wilson, indicated by (W), and Koster's Color Guide, indicated by (K). All observations were made from plants and flowers growing in greenhouse at Richmond, Ind.

*The plant*

Origin: Seedling (66–153Y).
Parentage: *Seed parent.*—Lydia (unpatented).
*Pollen parent.*—Golden Wave (P.P. 2,105).
Classification: *Botanic.*—Rose hybrid.
*Commercial.*—Hybrid tea.
Form: Bush.
Growth: Moderately free and vigorous.
Habit: Upright and much branched.
Main Stems: Color: (K) Sage Green, Plate #78, overlaid with streaks of Tobacco Brown, Plate #88.
*Thorns.*—Several, long and downwardly hooked with a short narrow base. Color: (K) Purplish Mauve, Plate #53.
*Hairs and prickles.*—None.
Branches: Color: (W) Spinach Green 0960.
*Thorns.*—Several, long and downwardly hooked with short narrow base. Color: (K) Violet, Plate #59, changing to (W) Pod Green 961/1 at tip.

*Hairs and prickles.*—None.
New shoots: Color: (W) Scheeles Green 860/3.
*Thorns.*—Several of medium length, hooked downward and having a short narrow base. Color: (W) Spinel Red 0023/1 at base gradually changing to Veronese Green 660/3 at tip.
*Hairs and prickles.*—None.
Foliage: Quantity—abundant
*Leaves.*—Shape—odd pinnate. Size—Medium large.
*Leaflets.*—5 to 7 in number. Shape: Elliptical, with acuminate apex, obtuse base and serrated margin. Texture: Heavy and leathery. Aspect: Glossy. Color: Young leaflets: Upper surface (W) Pea Green 61/1 overlaid with shades of Oxblood Red 00823/3. Under surface (W) Pea Green 61/3 with very light shades of Oxblood Red 00823/3. Mature leaflets: Upper surface (W) Spinach Green 0960 (nearest color). Under surface (W) Lavender Green 000761/1.
*Stipules.*—Medium in length and width with short points turning outward at an angle of less than 45°.
*Rachis.*—Heavy, with upper side grooved and under side prickly.

*The bud*

Before calyx breaks:
*Size.*—Medium large.
*Form.*—Ovoid, with conspicuous neck, foliaceous surface appendages, and slender foliaceous parts extending beyond bud tip a distance equal to ¼ or more of bud length.
*Color of calyx.*—(W) Scheeles Green 860/2.
As calyx breaks:
*Color of bud.*—(W) Aureolin 3/1.
As first petal opens:
*Bud size.*—Medium small.
*Bud form.*—Ovoid.
*Color of petal.*—Outside—(W) Lemon Yellow 4/1. Inside—(W) Aureolin 3/1.
*Opening.*—Bud opens up well.
Sepals: Permanent, spear shaped and moderately short.
*Color.*—Inside—(W) Scheeles Green 860/3 overlaid with white fuzz. Outside—(W) Scheeles Green 860/3.
*Peduncle.*—Strong and erect, of medium length and diameter. Bark: Smooth, with color of (W) Scheeles Green 860/2 and no thorns, prickles or hairs.

*The flower*

Blooming habit: Abundant and continuous.
Borne: Singly, on strong stems of medium length.
Size: Medium large. 2½ to 3½ inches in diameter.
Shape: Full and high centered at first with tightly and outwardly rolled petals, becoming globular at maturity with petals loosely rolled outwardly.
Petalage: Double with 30 to 35 petals regularly arranged.
*Shape.*—Outside and intermediate petals: Obovate with obtuse apex. Inside petals: Some obovate and some spatulate, all with obtuse apex.
*Color.*—(1) A newly opened flower in August 1972: Outside surface: Outside petals—(W) Mimosa Yellow 602; intermediate and inner petals—(W) (W) Aureolin 3/1. Inside surface:outside petals—(W) Aureolin 3/1 with some veins of Aureolin 3; intermediate petals—(W) Aureolin 3/1; inner petals—(W) Aureolin 3. (2) Bloom opened three days in August 1972: Outside surface: Outside petals—(W) Primrose Yellow 601/2; Intermediate and inner petals—(W) Mimosa Yellow 602/1; Inside surface: Outside petals—(W) Primrose Yellow 601/3 at tip, through 601/2 in body to 601/1 at base; intermediate and inner petals—(W) Sulphur Yellow 1/2 gradually changing to 1/1 at base.

*Texture.*—Moderately thick.

*Appearance.*—Inside—satiny. Outside—shiny.

*Persistence.*—Petals hang on.

Fragrance: Slight tea.

Lasting quality: As a cut flower—4 to 5 days at living room temperature.

General color effect of open bloom:

*Newly open.*—(W) Aureolin 3/1.

*Three days open.*—(W) Aureolin 3/2.

*Reproductive organs*

Stamens: Many in number arranged regularly about pistils.

*Anthers.*—Large in size, opening all at once. Color: Chinese Yellow (W) 606/1.

*Filaments.*—Medium length, most with anthers. Color: (K) Carmine, Plate No. 29.

*Pollen.*—Abundant and of Orange Buff (W–507/2) color.

Pistils: Many in number.

*Styles.*—Moderately thin, bunched and of medium, but uneven, length. Color: (W) Chartreuse Green 663/3.

*Stigmas.*—Color: (K) Rosy Pink, Plate No. 30.

Ovaries: Some protruding from calyx.

Hips: None.

The new variety of rose plant is an improvement over its seed parent Lydia in that it has a more vigorous growth habit and a more abundant flower production on longer, stronger stems. Also, this new variety is better than its pollen parent Golden Wave in that it propagates better, is mildew resistant, has a prolific growth habit, and its flower has a more constant intense color which does not fade under extreme temperatures or low light intensities. This new variety is to be further distinguished by its shiny dark green and leathery foliage which contrasts well with its yellow blossoms.

I claim:

1. A new and distinct variety of rose plant substantially as herein shown and described, characterized by the distinct intense yellow color of its blooms which does not fade, and by its abundant and continuous flower production under greenhouse culture.

No references cited.

ROBERT E. BAGWILL, Primary Examiner